(12) United States Patent
Parthasaradhi Reddy et al.

(10) Patent No.: US 8,912,333 B2
(45) Date of Patent: Dec. 16, 2014

(54) POLYMORPHS OF PITAVASTATIN CALCIUM

(75) Inventors: Bandi Parthasaradhi Reddy, Hyderabad (IN); Kura Rathnakar Reddy, Hyderabad (IN); Dasari Muralidhara Reddy, Hyderabad (IN); Samala Malla Reddy, Hyderabad (IN); Bandi Vamsi Krishna, Hyderabad (IN)

(73) Assignee: Hetero Research Foundation, Balanagar, Hyderabad (IN)

( * ) Notice: Subject to any disclaimer, the term of this patent is extended or adjusted under 35 U.S.C. 154(b) by 0 days.

(21) Appl. No.: 13/884,734

(22) PCT Filed: Aug. 23, 2011

(86) PCT No.: PCT/IN2011/000569
§ 371 (c)(1),
(2), (4) Date: May 10, 2013

(87) PCT Pub. No.: WO2012/063254
PCT Pub. Date: May 18, 2012

(65) Prior Publication Data
US 2013/0237563 A1    Sep. 12, 2013

(30) Foreign Application Priority Data
Nov. 12, 2010 (IN) .............. 3399/CHE/2010

(51) Int. Cl.
*C07D 215/04* (2006.01)
*C07D 215/16* (2006.01)

(52) U.S. Cl.
CPC ............ *C07D 215/04* (2013.01); *C07D 215/16* (2013.01)
USPC .......................................... 546/173; 514/312

(58) Field of Classification Search
CPC ...................................................... C07D 215/04
USPC .......................................... 546/173; 514/312
See application file for complete search history.

(56) References Cited

U.S. PATENT DOCUMENTS

| | | | |
|---|---|---|---|
| 5,753,675 A | 5/1998 | Wattanasin | |
| 5,856,336 A | 1/1999 | Fujikawa et al. | |
| 7,064,209 B2 * | 6/2006 | Horiuchi et al. | 546/173 |
| 7,241,800 B2 | 7/2007 | Huang | |
| 8,487,105 B2 * | 7/2013 | Reddy et al. | 546/173 |
| 2005/0282883 A1 | 12/2005 | Griffen et al. | |
| 2007/0054947 A1 | 3/2007 | Cohen et al. | |
| 2008/0300406 A1 | 12/2008 | Casar | |
| 2009/0182008 A1 | 7/2009 | Van Der Schaaf et al. | |

FOREIGN PATENT DOCUMENTS

| | | |
|---|---|---|
| WO | WO-2004/072040 A1 | 8/2004 |
| WO | WO-2005/063711 A1 | 7/2005 |
| WO | WO-2007/132482 A2 | 11/2007 |
| WO | WO-2010/077062 A2 | 7/2010 |

OTHER PUBLICATIONS

International Search Report for PCT/IN2011/000569.

* cited by examiner

*Primary Examiner* — D Margaret M Seaman
(74) *Attorney, Agent, or Firm* — Choate Hall & Stewart LLP; Charles E. Lyon; Thomas H. McLean

(57) ABSTRACT

The present invention provides a solid of pitavastatin tert-butyl ester and process for its preparation. The present invention also provides a novel crystalline form of pitavastatin calcium, process for its preparation and pharmaceutical compositions comprising it.

28 Claims, 2 Drawing Sheets

POLYMORPHS OF PITAVASTATIN CALCIUM

CROSS-REFERENCE TO RELATED APPLICATIONS

The present application a 371 of Indian Patent Application No. 3399/CHE/2010, filed on Nov. 12, 2010 under the provisions of 35 U.S.C. §119 and the International Convention for the protection of Industrial Property, which are incorporated herein by reference in their entirety.

FIELD OF THE INVENTION

The present invention provides a solid of pitavastatin tert-butyl ester and process for its preparation. The present invention also provides a novel crystalline form of pitavastatin calcium, process for its preparation and pharmaceutical compositions comprising it.

BACKGROUND OF THE INVENTION

Pitavastatin is chemically, (3R,5S,6E)-7-[2-cyclopropyl-4-(4-fluorophenyl)-3-quinolinyl]-3,5-dihydroxy-6-heptenoic acid and has the structural formula:

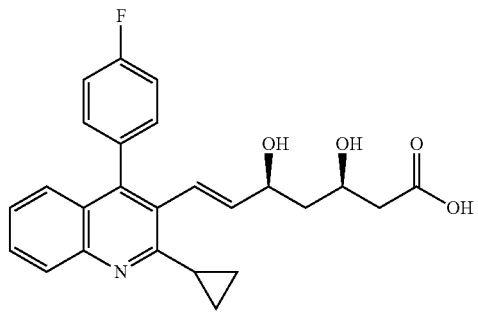 [SMILES: O=C(O)C[C@H](O)C[C@H](O)/C=C/c1c(C2CC2)nc2ccccc2c1-c1ccc(F)cc1]

Pitavastatin calcium is a novel member of the medication class of statins. Marketed in the United States under the trade name Livalo, it is like other statin drugs an inhibitor of HMG-CoA reductase, the enzyme that catalyses the first step of cholesterol synthesis. It is likely that pitavastatin will be approved for use in hypercholesterolaemia (elevated levels of cholesterol in the blood) and for the prevention of cardiovascular disease outside South and Southeast Asia as well.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining one polymorphic Form over the other.

Pitavastatin and its calcium salt can exist in different polymorphic Forms, which may differ from each other in terms of stability, physical properties, spectral data and methods of preparation.

Pitavastatin and its process were disclosed in U.S. Pat. No. 5,753,675.

Pitavastatin calcium and its process were disclosed in U.S. Pat. No. 5,856,336.

PCT publication no. WO 2004/072040 (herein after referred to '040 patent) disclosed crystalline polymorph A, polymorph B, polymorph C, polymorph D, polymorph E, polymorph F and amorphous form of pitavastatin calcium.

According to the '040 patent, crystalline polymorph A of pitavastatin calcium was characterized by an X-ray powder diffraction pattern having peaks expressed as 2θ at about 5.0, 6.8, 9.1, 10.0, 10.5, 11.0, 13.3, 13.7, 14.0, 14.7, 15.9, 16.9, 17.1, 18.4, 19.1, 20.8, 21.1, 21.6, 22.9, 23.7, 24.2, 25.2, 27.1, 29.6, 30.2 and 30.2 degrees.

According to the '040 patent, crystalline polymorph B of pitavastatin calcium was characterized by an X-ray powder diffraction pattern having peaks expressed as 2θ at about 4.6, 5.3, 6.2, 7.7, 9.2, 9.6, 10.3, 11.3, 11.7, 12.6, 13.0, 13.9, 14.7, 14.9, 15.6, 16.3, 17.0, 17.4, 18.0, 18.7, 19.3, 20.0, 20.5, 20.8, 21.2, 21.5, 22.4, 23.2, 23.8, 24.4, 25.2, 26.0, 26.4, 27.0, 27.9 and 28.9 degrees.

According to the '040 patent, crystalline polymorph C of pitavastatin calcium was characterized by an X-ray powder diffraction pattern having peaks expressed as 2θ at about 4.1, 5.6, 7.8, 8.3, 10.3, 11.6, 17.5, 17.9, 18.7, 19.5, 20.6, 21.5, 21.9, 23.1, 24.0 and 24.8 degrees.

According to the '040 patent, crystalline polymorph D of pitavastatin calcium was characterized by an X-ray powder diffraction pattern having peaks expressed as 2θ at about 5.0, 6.5, 6.8, 8.7, 10.0, 10.2, 10.8, 13.1, 13.5, 14.3, 15.3, 16.1, 16.8, 18.2, 18.5, 19.0, 19.9, 20.5, 21.0, 21.7, 22.3, 23.4, 24.0, 25.6 and 26.2 degrees.

According to the '040 patent, crystalline polymorph E of pitavastatin calcium was characterized by an X-ray powder diffraction pattern having peaks expressed as 2θ at about 4.4, 5.0, 6.6, 6.8, 8.9, 10.0, 10.3, 10.8, 13.3, 13.6, 14.0, 15.2, 15.9, 16.4, 16.9, 17.8, 18.3, 18.9, 20.2, 20.4, 20.7, 20.9, 21.1, 21.6, 21.7, 22.3, 23.5, 23.8, 24.1, 24.7, 25.4, 26.6, 30.2 and 34.0 degrees.

According to the '040 patent, crystalline polymorph F of pitavastatin calcium was characterized by an X-ray powder diffraction pattern having peaks expressed as 2θ at about 5.1, 5.6, 7.0, 8.8, 9.6, 10.2, 10.9, 11.3, 11.9, 12.5, 13.0, 13.7, 14.4, 14.7, 15.3, 15.5, 16.8, 17.6, 18.3, 19.3, 19.7, 20.6, 21.2, 21.8, 22.8, 23.1, 23.8, 24.1, 24.8, 25.7, 26.2, 26.6, 26.9, 28.4, 29.5, 29.8 and 30.9 degrees.

PCT publication no. WO 2005/063711 disclosed crystal form A of pitavastatin calcium which contains from 5 to 15% of water.

PCT publication no. WO 2007/132482 disclosed a process for the preparation of pitavastatin calcium. According to this process, pitavastatin calcium can be prepared by reacting the (4R,6S)-(E)-6-[2-(2-cyclopropyl-4-(4-fluorophenyl)quinoline-3-yl)-vinyl]-2,2-dimethyl-1,3-dioxane-4-yl}acetic acid tertiary butyl ester in acetonitrile with hydrochloric acid and then treating with sodium hydroxide. The reaction mixture obtained was further treated with methyl amine to form pitavastatin methyl amine salt and then converted to pitavastatin calcium.

PCT publication no. WO 2010/077062 described a process for the preparation of pitavastatin calcium. According to this process, pitavastatin calcium can be prepared by reacting the tert-butyl (3R,5S,6E)-7-[2-cyclopropyl-4-(4-fluorophenyl)quinolin-3-yl]-3,5-O-isopropylidene-3,5-dihydroxy-6-heptenoate in acetonitrile with hydrochloric acid and then treating with sodium hydroxide. The reaction mixture obtained was further treated with calcium chloride dihydrate to form pitavastatin calcium.

Tert-butyl-(3R,5S,E)-7-(2-chloropropyl-4-(4-fluorophenyl)quinolin-3-yl)-3,5-dihydroxyhept-6-enoate (pitavastatin tert-butyl ester) is a key intermediate for the preparation of pitavastatin calcium. The chemical formula of pitavastatin tert-butyl ester may be represented as:

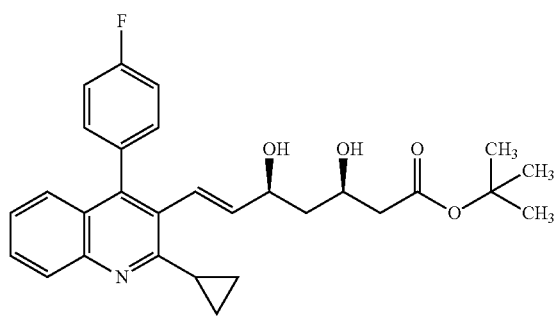 [SMILES: CC(C)(C)OC(=O)C[C@H](O)C[C@H](O)/C=C/c1c(C2CC2)nc2ccccc2c1-c1ccc(F)cc1]

The process for the preparation of solid of pitavastatin tert-butyl ester was not disclosed in the prior art. We have discovered that pitavastatin tert-butyl ester can be obtained as a solid. It has been found that the pitavastatin or pharmaceutical acceptable salt of it can be obtained with good chromatographic purity and good yields when the crystalline solid of pitavastatin tert-butyl ester is used for the preparation of the said compounds.

We have also discovered novel crystalline form of pitavastatin calcium. The novel form has been found to be stable over the time and reproducible and so, suitable for pharmaceutical preparations.

Thus, one object of the present invention is to provide a solid of pitavastatin tert-butyl ester and process for its preparation.

Another object of the present invention is to provide a novel crystalline form of pitavastatin calcium, process for its preparation and pharmaceutical compositions comprising it.

SUMMARY OF THE INVENTION

In one aspect, the present invention provides a solid of pitavastatin tert-butyl ester.

In another aspect, the present invention provides a process for the preparation of solid of pitavastatin tert-butyl ester, which comprises:
 a) reacting R-(−)-camphor sulfonic acid with tert-butyl-(3R,5S,6Z)-7-{2-cyclopropyl-4-(4-fluorophenyl)quinoline-3-yl}-3,5-isopropylidenedioxy-6-heptenoate in an nitrile solvent and water;
 b) adding a mixture of water and a solvent selected from an ester solvent, an chlorinated solvent, an ether solvent or mixture thereof;
 c) concentrating the reaction mass;
 d) adding hydrocarbon solvent to the residual mass obtained in step (c); and
 e) isolating solid of pitavastatin tert-butyl ester.

In another aspect, the present invention provides a crystalline form of pitavastatin calcium designated as form H1 characterized by peaks in the powder x-ray diffraction spectrum having 2θ angle positions at about 4.9, 6.9, 10.9, 14.8, 15.3, 16.6, 17.7, 19.1, 19.5, 19.9, 20.3, 21.0 and 21.8±0.2 degrees.

In another aspect, the present invention provides a process for the preparation of pitavastatin calcium crystalline form H1, which comprises:
 a) providing a solution of pitavastatin calcium in an alcoholic solvent, a ketonic solvent, an ester solvent or a mixture thereof;
 b) heating the solution obtained in step (a) at reflux;
 c) cooling the reaction mass obtained in step (b) at below 30° C.; and
 d) isolating pitavastatin calcium crystalline form H1.

In yet another aspect, the present invention provides a pharmaceutical composition comprising crystalline form H1 of pitavastatin calcium and pharmaceutically acceptable excipients.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.02 degrees two theta per step and a step time of 10.8 seconds. The sample was simply placed on the sample holder. The sample was rotated at 30 rpm at a voltage 40 KV and current 35 mA.

DETAILED DESCRIPTION OF THE INVENTION

The term "room temperature" refers to temperature at about 20 to 30° C.

According to one aspect of the present invention, there is provided a solid of pitavastatin tert-butyl ester.

Figure 1:
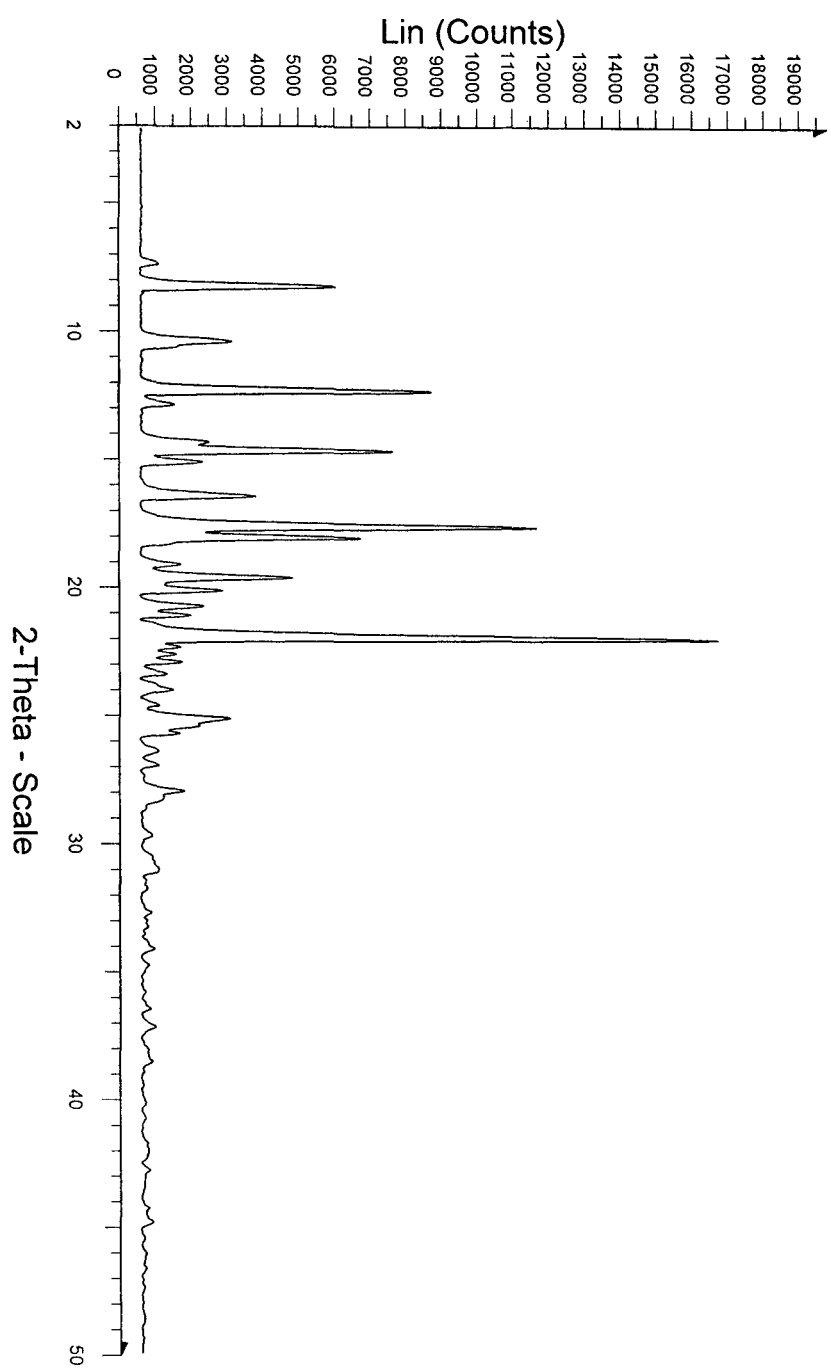
FIG. 1 is an X-ray powder diffraction spectrum of solid of pitavastatin tert-butyl ester.

The solid of pitavastatin tert-butyl ester may preferably be crystalline solid. Typically powdered x-ray diffractogram (PXRD) of solid of pitavastatin tert-butyl ester is shown in FIG. 1.

According to another aspect of the present invention, there is provided a process for the preparation of solid of pitavastatin tert-butyl ester, which comprises:
 a) reacting R-(−)-camphor sulfonic acid with tert-butyl-(3R,5S,6Z)-7-{2-cyclopropyl-4-(4-fluorophenyl)quinoline-3-yl}-3,5-isopropylidenedioxy-6-heptenoate in an nitrile solvent and water;
 b) adding a mixture of water and a solvent selected from an ester solvent, an chlorinated solvent, an ether solvent or mixture thereof;
 c) concentrating the reaction mass;
 d) adding hydrocarbon solvent to the residual mass obtained in step (c); and
 e) isolating solid of pitavastatin tert-butyl ester.

The nitrile solvent used in step (a) may preferably be a solvent or mixture of solvents selected from acetonitrile, propionitrile, butyronitrile and benzonitrile, and more preferable nitrile solvent is acetonitrile.

The reaction in step (a) may conveniently be carried out at room temperature.

Preferably the ester solvent used in step (b) may be selected from ethyl acetate, methyl acetate, isopropyl acetate, tert-butyl methyl acetate and ethyl formate. More preferably the ester solvent is ethyl acetate.

The chlorinated solvent used in step (b) may preferably be selected from methylene chloride, chloromethane, dichloroethane, chloroform, carbon tetrachloride and chlorobenzene, and more preferably the chlorinated solvent is methylene chloride.

The ether solvent used in step (b) may preferably be selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane, and more preferably the ether solvent is methyl tert-butyl ether.

Preferably the reaction mass is concentrated in step (c) by distilling off the solvent. The distilling off the solvent may be carried out at atmospheric pressure or at reduced pressure. The distillation may preferably be carried out until the solvent is almost completely distilled off.

The hydrocarbon solvent used in step (d) may preferably be a solvent or mixture of solvents selected from cyclohexane, hexane, n-heptane, benzene, toluene and xylene, and more preferably the hydrocarbon solvent is hexane.

Solid of pitavastatin tert-butyl ester may be isolated in step (e) by methods known such as filtration or centrifugation.

Figure 2:
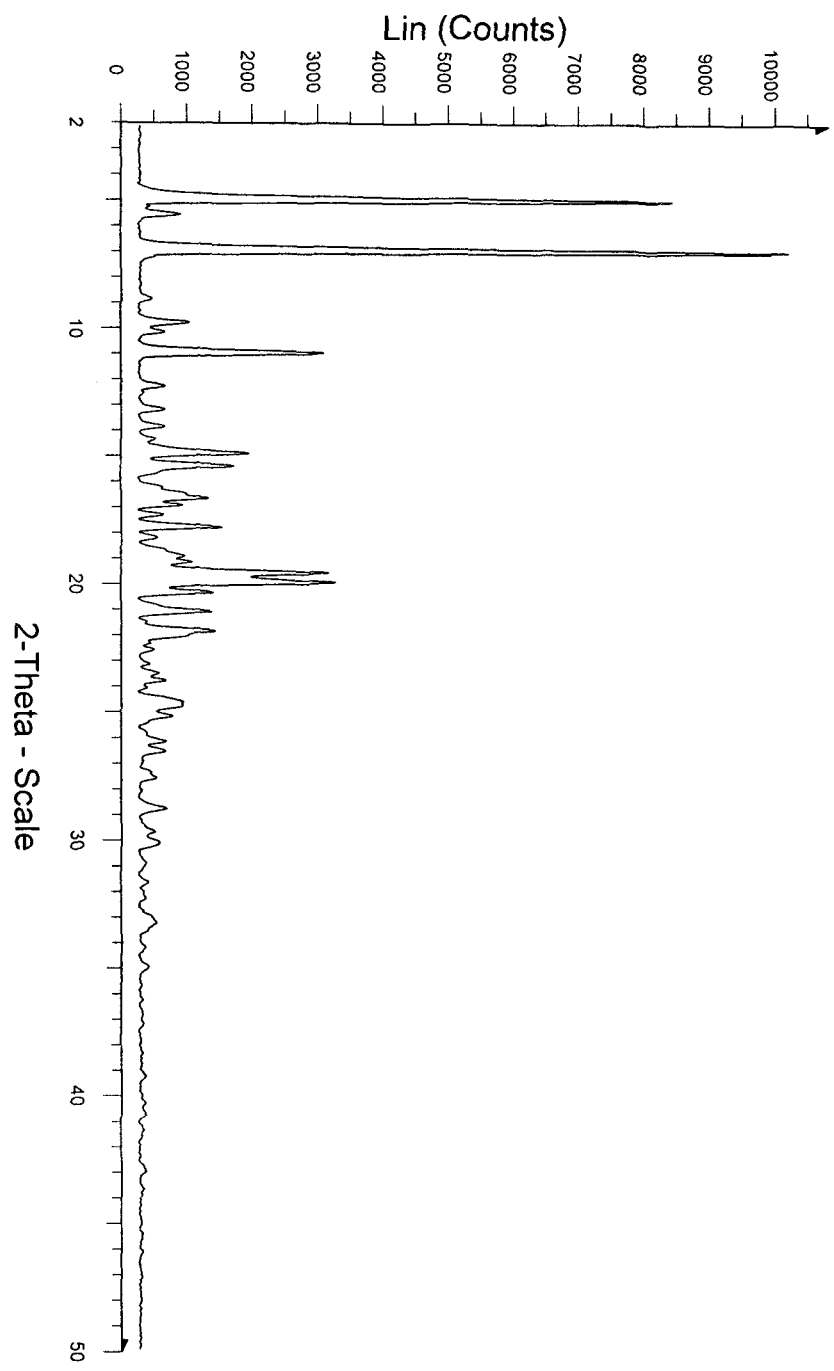
FIG. 2 is an X-ray powder diffraction spectrum of pitavastatin calcium crystalline form H1.

According to another aspect of the present invention, there is provided a crystalline form of pitavastatin calcium designated as form H1 characterized by peaks in the powder x-ray diffraction spectrum having 2θ angle positions at about 4.9, 6.9, 10.9, 14.8, 15.3, 16.6, 17.7, 19.1, 19.5, 19.9, 20.3, 21.0 and 21.8±0.2 degrees. The powdered x-ray diffractogram (PXRD) of pitavastatin calcium crystalline form H1 is shown in FIG. 2.

The pitavastatin calcium crystalline form H1 may be identified and differentiated from the known polymorphs by its characteristic PXRD pattern. Thus, for example, peaks at 6.2 and 7.7 degrees 2θ are absent in the PXRD of the pitavastatin calcium crystalline form H1 of the present invention, but are present in the PXRD of the pitavastatin calcium crystalline polymorph B disclosed in the '040 patent. Similarly, a peak at 6.5 degrees 2θ is absent in the PXRD of the crystalline form H1 of the present invention, but is present in the PXRD of the pitavastatin calcium crystalline polymorph D disclosed in the '040 patent. Similarly, a peak at 6.6 degrees 2θ is absent in the PXRD of the crystalline form H1 of the present invention, but is present in the PXRD of the pitavastatin calcium crystalline polymorph E disclosed in the '040 patent.

According to another aspect of the present invention, there is provided a process for the preparation of pitavastatin calcium crystalline form H1, which comprises:
a) providing a solution of pitavastatin calcium in an alcoholic solvent, a ketonic solvent, an ester solvent or a mixture thereof;
b) heating the solution obtained in step (a) at reflux;
c) cooling the reaction mass obtained in step (b) at below 30° C.; and
d) isolating pitavastatin calcium crystalline form H1.

The alcoholic solvent used in step (a) may preferably be a solvent or mixture of solvents selected from methanol, ethanol, isopropyl alcohol, tert-butyl alcohol, n-butanol and isobutyl alcohol. More preferably the alcoholic solvents are methanol, ethanol and isopropyl alcohol.

Preferably the ketonic solvent used in step (a) may preferably be a solvent or mixture of solvents selected from acetone, methyl ethyl ketone, methyl isobutyl ketone and diethyl ketone, and more preferably the ketonic solvent is acetone.

The ester solvent used in step (a) may preferably be a solvent or mixture of solvents selected from ethyl acetate, methyl acetate, isopropyl acetate, tert-butyl methyl acetate and ethyl formate. More preferably the ester solvents are ethyl acetate and isopropyl acetate.

The step (c) may preferably be carried out at about 0 to 25° C., and more preferably at about 0 to 5° C.

Isolation of pitavastatin calcium crystalline form H1 in step (d) may preferably be performed by conventional techniques such as centrifugation and filtration.

According to another aspect of the present invention, there is provided a pharmaceutical composition comprising crystalline form H1 of pitavastatin calcium and pharmaceutically acceptable excipients, and optionally other therapeutic ingredients. The crystalline form H1 may preferable be formulated into tablets, capsules, suspensions, dispersions, injectables and other pharmaceutical forms.

The invention will now be further described by the following examples, which are illustrative rather than limiting.

EXAMPLES

Example 1

Preparation of tert-butyl-2-((4R,6S)-6-((E)-2-(2-cyclopropyl-4-(4-fluorophenyl)quinolin-3-yl)vinyl)-2,2-dimethyl-1,3-dioxan-4-yl)acetate Step-I: Preparation of (2-cyclopropyl-4-(4-fluorophenyl)quinolin-3-yl)methanol 2-Cyclopropyl-4-(4-fluorophenyl)quinoline-3-carbaldehyde (30 gm) was added methanol (30 ml) and tetrahydrofuran (270 ml) at room temperature. The reaction mixture was then cooled to 0° C. and then added sodium borohydride (5.8 gm) for 30 minutes at 0 to 5° C. The reaction mass was stirred for 1 hour 30 minutes and then added water (150 ml) and ethyl acetate (150 ml). The reaction mass was stirred for 10 minutes, and then the layers were separated and the aqueous layer was extracted with ethyl acetate. The combined organic layers were dried with sodium sulfate and then concentrated to obtain a residual solid. To the residual solid was added n-hexane (150 ml) and stirred for 30 minutes. The separated solid was filtered and dried to obtain 29 gm of (2-cyclopropyl-4-(4-fluorophenyl)quinolin-3-yl)methanol.

Step-II: Preparation of 3-(bromomethyl)-2-cyclopropyl-4-(4-fluorophenyl)quinoline (2-Cyclopropyl-4-(4-fluorophenyl)quinolin-3-yl)methanol (42 gm) as obtained in step-I was dissolved in methylene dichloride (630 ml) and stirred for 10 minutes. The solution was then cooled to 0 to 5° C. and then added phosphorus tribromide (11.4 ml) and stirred for 10 minutes at 0 to 5° C. The temperature of the reaction mass was raised to room temperature and stirred for 3 hours at room temperature. The reaction mass was quenched with saturated aqueous potassium bromide solution (700 ml) and then the layers were separated. The aqueous layer was extracted with methylene chloride and the combined organic layers were dried with sodium sulfate and then concentrated to obtain 40 gm of 3-(bromomethyl)-2-cyclopropyl-4-(4-fluorophenyl)quinoline.

Step-III: Preparation of {2-cyclopropyl-4-(4-fluorophenyl)quinolin-3-yl}methyl-triphenylphosphonium bromide 3-(Bromomethyl)-2-cyclopropyl-4-(4-fluorophenyl)quinoline (24 gm) as obtained in step-II was dissolved in methylene chloride (360 ml) and stirred for 15 minutes. To the solution was added triphenylphosphine (17.7 gm) and stirred for 10 minutes. The contents were then heated reflux and maintained for 4 hours at reflux. The reaction mass was cooled to room temperature and then concentrated to obtain a residual mass. To the residual mass was added toluene (240 ml) and stirred for 2 hours at room temperature. The separated solid was filtered and dried to get a solid. The solid obtained was dissolved in methylene chloride (500 ml) and water (250 ml) and then the layers were separated. The organic layer was dried with sodium sulfate and then concentrated to get a solid. The obtained solid was washed with n-hexane and dried to obtain 40 gm of {2-cyclopropyl-4-(4-fluorophenyl)quinolin-3-yl}methyltriphenylphosphonium-bromide.

Step-IV: Preparation of tert-butyl-(3R,5S,6Z)-7-{2-cyclopropyl-4-(4-fluorophenyl)-quinoline-3-yl}-3,5-isopropylidenedioxy-6-heptenoate {2-Cyclopropyl-4-(4-fluorophenyl)quinolin-3-yl}methyltriphenylphosphonium-bromide (50 gm) as obtained in step-III was dissolved in dimethylformamide (750 ml) and stirred for 15 minutes to obtain a solution. To the solution was added potassium carbonate (22.3 gm) and then added a solution of tert-butyl-2-(4R,6S)-6-formyl-2,2-dimethyl-1,3-dioxan-4-yl)acetate (25.1 gm) in dimethylformamide (50 ml) slowly at room temperature. The reaction mixture was heated to 80° C. and stirred for 5 hours. The reaction mass was then cooled to room temperature and then added toluene (300 ml) and water (300 ml). Then the layers were separated and the aqueous layer was extracted with toluene. The combined organic layers were dried with sodium sulfate and then concentrated to obtain a residual mass. To the residual mass was added n-hexane (220 ml) and stirred for 1 hour. The reaction mass was filtered to remove unwanted solid and then concentrated the n-hexane layer to obtain a residual solid. To the residual solid obtained was added 30% aqueous acetonitrile (500 ml) and then cooled to 0° C. The reaction mass was maintained for 3 hours 30 minutes and filtered. The solid obtained was dried to give 32 gm of tert-butyl-(3R,5S,6Z)-7-{2-cyclopropyl-4-(4-fluorophenyl)quinoline-3-yl}-3,5-isopropylidenedioxy-6-heptenoate.

Example 2

Preparation of tert-butyl-(3R,5S,E)-7-(2-chloropropyl-4-(4-fluorophenyl)quinolin-3-yl)-3,5-dihydroxy-hept-6-enoate (pitavastatin tert-butyl ester)

Tert-butyl-(3R,5S,6Z)-7-{2-cyclopropyl-4-(4-fluorophenyl)quinoline-3-yl}-3,5-isopropylidenedioxy-6-heptenoate (47 gm) as obtained in example 1 was added to acetonitrile (470 ml) and stirred for 15 minutes. To the reaction mixture was added water (47 ml) and then added R-(-)-camphor sulfonic acid (25.3 gm) at room temperature. The reaction mass was maintained for 4 hours at room temperature and then added ethyl acetate (300 ml) and water (500 ml). Then the layers were separated and the aqueous layer was extracted with ethyl acetate. The combined organic layers were dried with sodium sulfate and the solvent was distilled off under reduced pressure to obtain a crude solid. To the crude solid was added n-hexane (200 ml) and stirred for 30 minutes. The solid obtained was collected by filtration and dried to obtain 35 gm of pitavastatin tert-butyl ester (P-XRD of the solid obtained is shown in FIG. 1).

Example 3

Preparation of Pitavastatin Calcium

Step-I: Preparation of Pitavastatin Phenylethylamine Salt

Pitavastatin tert-butyl ester (22 gm) as obtained in example 2 was added acetonitrile (174 ml) and then added hydrochloric acid (4N; 150 ml) slowly at room temperature. The reaction mixture was stirred for 3 hours and then added 10% sodium hydroxide (392 ml) at room temperature. The reaction mixture was stirred for 1 hour at room temperature and then added sodium chloride (500 gm). The pH of the reaction mass was adjusted to 3.0 to 4.0 with hydrochloric acid (1N) at 0° C. and then extracted with ethyl acetate. The combined organic layers were dried with sodium sulfate and then concentrated to obtain a residual solid. The residual solid was dissolved in methylene chloride (100 ml) and then added (R)-phenylethylamine (7 ml) slowly at room temperature. The reaction mixture was stirred for 36 hours at room temperature and filtered. The solid obtained was dried to get pitavastatin phenylethylamine salt.

Step-II: Preparation of Pitavastatin Calcium

Pitavastatin phenylethylamine salt (12.6 gm) as obtained in step-I was added to a mixture of water (163 ml) and ethanol (126 ml). The reaction mixture was cooled to 0° C. and then added aqueous sodium hydroxide solution (1 gm in 189 ml of water) slowly. The reaction mixture was stirred for 2 hours at 0° C. and filtered on vacuum pump. The filtrate obtained was then concentrated to obtain a residual mass and then added aqueous calcium chloride solution (4.76 gm in 189 ml of water) slowly for 2 hours at 0° C. The reaction mass was stirred for 12 hours and filtered. The solid obtained was dried under vacuum at 40° C. for 16 hours to obtain 9.6 gm of pitavastatin calcium

Example 4

Preparation of Pitavastatin Calcium Crystalline Form H1

Pitavastatin calcium (5 gm) as obtained in example 3 was dissolved in isopropyl acetate (50 ml) and then heated to reflux. The reaction mass was maintained for 4 hours at reflux and then cooled to room temperature. The reaction mass was stirred for 1 hour at room temperature. The contents were further cooled to 0° C. and stirred for 15 minutes. The separated solid was filtered and dried to obtain 4.8 gm of pitavastatin calcium crystalline form H1.

Example 5

Preparation of Pitavastatin Calcium Crystalline Form H1

Pitavastatin calcium (5 gm) was dissolved in a mixture of isopropyl acetate and ethyl acetate (2:1; 50 ml) and then heated to reflux. The reaction mass was maintained for 8 hours at reflux and then cooled to room temperature. The reaction mass was stirred for 72 hours at room temperature and filtered. The solid obtained was dried to get 4.6 gm of pitavastatin calcium crystalline form H1.

Example 6

Preparation of Pitavastatin Calcium Crystalline Form H1

Pitavastatin calcium (10 gm) was dissolved in a mixture of isopropyl acetate and ethyl acetate (9:1; 100 ml) and then heated to reflux. The reaction mass was maintained for 8 hours at reflux and then cooled to room temperature. The reaction mass was stirred for 70 hours at room temperature and filtered. The solid obtained was dried to get 9.0 gm of pitavastatin calcium crystalline form H1.

Example 7

Preparation of Pitavastatin Calcium Crystalline Form H1

Pitavastatin calcium (10 gm) was dissolved in a mixture of isopropyl acetate and ethyl acetate (1:1; 100 ml) and then heated to reflux. The reaction mass was maintained for 8 hours at reflux and then cooled to room temperature. The reaction mass was stirred for 68 hours at room temperature and filtered. The solid obtained was dried to get 8.9 gm of pitavastatin calcium crystalline form H1.

Example 8

Preparation of Pitavastatin Calcium Crystalline Form H1

Pitavastatin calcium (10 gm) was dissolved in a mixture of ethanol and ethyl acetate (4:1; 100 ml) and then heated to reflux. The reaction mass was maintained for 6 hours at reflux and then cooled to room temperature. The reaction mass was stirred for 48 hours at room temperature. The contents were further cooled to 0° C. and stirred for 30 minutes. The separated solid was filtered and dried to obtain 9.3 gm of pitavastatin calcium crystalline form H1.

Example 9

Preparation of Pitavastatin Calcium Crystalline Form H1

Pitavastatin calcium (10 gm) was dissolved in a mixture of ethanol and isopropyl acetate (2:1; 100 ml) and then heated to reflux. The reaction mass was maintained for 6 hours at reflux and then cooled to room temperature. The reaction mass was stirred for 40 hours at room temperature. The contents were further cooled to 0° C. and stirred for 30 minutes, filtered. The solid obtained was dried to get 9.1 gm of pitavastatin calcium crystalline form H1.

Example 10

Preparation of Pitavastatin Calcium Crystalline Form H1

Pitavastatin calcium (10 gm) was dissolved in a mixture of acetone and methanol (1:1; 100 ml) and then heated to reflux. The reaction mass was maintained for 7 hours at reflux and then cooled to room temperature. The reaction mass was stirred for 42 hours at room temperature. The contents were further cooled to 0° C. and stirred for 30 minutes, filtered. The solid obtained was dried to get 9.0 gm of pitavastatin calcium crystalline form H1.

Example 11

Preparation of Pitavastatin Calcium Crystalline Form H1

Pitavastatin calcium (10 gm) was dissolved in a mixture of ethanol and isopropyl acetate (1:9; 100 ml) and then heated to reflux. The reaction mass was maintained for 6 hours at reflux and then cooled to room temperature. The reaction mass was stirred for 40 hours at room temperature. The contents were further cooled to 0° C. and stirred for 30 minutes, filtered. The solid obtained was dried to get 9.1 gm of pitavastatin calcium crystalline form H1.

Example 12

Preparation of Pitavastatin Calcium Crystalline Form H1

Example 11 was repeated using methanol solvent instead of ethanol solvent to obtain pitavastatin calcium crystalline form H1.

Example 13

Preparation of Pitavastatin Calcium Crystalline Form H1

Example 11 was repeated using isopropyl alcohol solvent instead of ethanol solvent to obtain pitavastatin calcium crystalline form H1.

We claim:
1. A process for the preparation of solid of pitavastatin tert-butyl ester, which comprises:
 a. reacting R-(-)-camphor sulfonic acid with tert-butyl-(3R,5S,6Z)-7-{2-cyclopropyl-4-(4-fluorophenyl) quinoline-3-yl}-3,5-isopropylidenedioxy-6-heptenoate in a nitrile solvent and water;
 b. adding a mixture of water and a solvent selected from an ester solvent, a chlorinated solvent, an ether solvent or mixture thereof;
 c. concentrating the reaction mass;
 d. adding hydrocarbon solvent to the residual mass obtained in step (c); and
 e. isolating solid pitavastatin tert-butyl ester.
2. The process as claimed in claim 1, wherein the nitrile solvent used in step (a) is a solvent or mixture of solvents selected from acetonitrile, propionitrile, butyronitrile and benzonitrile.
3. The process as claimed in claim 2, wherein the nitrile solvent is acetonitrile.
4. The process as claimed in claim 1, wherein the reaction in step (a) is carried out at room temperature.
5. The process as claimed in claim 1, wherein the ester solvent used in step (b) is a solvent or mixture of solvents selected from ethyl acetate, methyl acetate, isopropyl acetate, tert-butyl methyl acetate and ethyl formate.
6. The process as claimed in claim 5, wherein the ester solvent is ethyl acetate.
7. The process as claimed in claim 1, wherein the chlorinated solvent used in step (b) is selected from methylene chloride, chloromethane, dichloroethane, chloroform, carbon tetrachloride and chlorobenzene.

8. The process as claimed in claim 7, wherein the chlorinated solvent is methylene chloride.

9. The process as claimed in claim 1, wherein the ether solvent used in step (b) is selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane.

10. The process as claimed in claim 9, wherein the ether solvent is methyl tert-butyl ether.

11. The process as claimed in claim 1, wherein the hydrocarbon solvent used in step (d) is a solvent or mixture of solvents selected from cyclohexane, hexane, n-heptane, benzene, toluene and xylene.

12. The process as claimed in claim 11, wherein the hydrocarbon solvent is hexane.

13. A pitavastatin calcium crystalline form H1, characterized by peaks in the powder x-ray diffraction spectrum having 2θ angle positions at about 4.9, 6.9, 10.9, 14.8, 15.3, 16.6, 17.7, 19.1, 19.5, 19.9, 20.3, 21.0 and 21.8±0.2 degrees.

14. A pitavastatin calcium crystalline form H1, characterized by an x-ray powder diffractogram as shown in FIG. 2.

15. A process for the preparation of pitavastatin calcium crystalline form H1 as claimed in claim 13, which comprises:
   a. providing a solution of pitavastatin calcium in an alcoholic solvent, a ketonic solvent, an ester solvent or a mixture thereof;
   b. heating the solution obtained in step (a) at reflux;
   c. cooling the reaction mass obtained in step (b) at below 30° C.; and
   d. isolating pitavastatin calcium crystalline form H1.

16. The process as claimed in claim 15, wherein the alcoholic solvent used in step (a) is a solvent or mixture of solvents selected from methanol, ethanol, isopropyl alcohol, tert-butyl alcohol, n-butanol and isobutyl alcohol.

17. The process as claimed in claim 16, wherein the alcoholic solvent used in step (a) is a solvent or a mixture of solvents selected from methanol, ethanol and isopropyl alcohol.

18. The process as claimed in claim 15, wherein the ketonic solvent used in step (a) is a solvent or mixture of solvents selected from acetone, methyl ethyl ketone, methyl isobutyl ketone and diethyl ketone.

19. The process as claimed in claim 18, wherein the ketonic solvent is acetone.

20. The process as claimed in claim 15, wherein the ester solvent used in step (a) is a solvent or mixture of solvents selected from ethyl acetate, methyl acetate, isopropyl acetate, tert-butyl methyl acetate and ethyl formate.

21. The process as claimed in claim 20, wherein the ester solvent used in step (a) is a solvent or mixture of solvents selected from ethyl acetate and isopropyl acetate.

22. The process as claimed in claim 15, wherein step (c) is carried out at about 0 to 25° C.

23. The process as claimed in claim 22, wherein step (c) is carried out at about 0 to 5° C.

24. A pharmaceutical composition that comprises crystalline form H1 of pitavastatin calcium and pharmaceutically acceptable excipients.

25. The pharmaceutical composition as claimed in claim 24, wherein the crystalline form is formulated into a tablet, capsule, suspension, dispersion, injectable, or other pharmaceutical form.

26. The pharmaceutical composition of claim 24, further comprising other therapeutic ingredients.

27. The pharmaceutical composition of claim 24, wherein the crystalline form H1 is characterized by peaks in the powder x-ray diffraction spectrum having 2θ angle positions at about 4.9, 6.9, 10.9, 14.8, 15.3, 16.6, 17.7, 19.1, 19.5, 19.9, 20.3, 21.0 and 21.8±0.2 degrees.

28. The pharmaceutical composition of claim 24, wherein the crystalline form H1 is characterized by an x-ray powder diffractogram as shown in FIG. 2.

* * * * *